(12) United States Patent
Galehr et al.

(10) Patent No.: US 6,857,805 B2
(45) Date of Patent: Feb. 22, 2005

(54) APPLICATION APPARATUS FOR HOLDING IN READINESS A SUBSTANCE TO BE APPLIED

(75) Inventors: Klaus Galehr, Schlins (AT); Frank Muller, Feldkirch (AT); Joanna Claire Todd, Feldkirch (AT); Roland Neubert, Tosters (AT); Alexander Huwig, Horgen (CH)

(73) Assignee: Ivoclar Vivadeut A.G., Schaan (LI)

( * ) Notice: Subject to any disclaimer, the term of this patent is extended or adjusted under 35 U.S.C. 154(b) by 0 days.

(21) Appl. No.: 10/653,822

(22) Filed: Sep. 3, 2003

(65) Prior Publication Data

US 2004/0184866 A1 Sep. 23, 2004

(30) Foreign Application Priority Data

Mar. 20, 2003 (DE) .......................... 103 12 454

(51) Int. Cl.⁷ .............................................. A46B 11/00
(52) U.S. Cl. ........................ 401/125; 401/123; 401/131
(58) Field of Search ................................ 401/123, 125, 401/131, 129, 130; 206/15.3, 209, 229, 484

(56) References Cited

U.S. PATENT DOCUMENTS

| 545,949 | A | * | 9/1895 | Dodge .......................... 401/125 |
| 675,970 | A | * | 6/1901 | Raymond, 2d. ............. 401/125 |
| 727,785 | A | * | 5/1903 | Gordon ....................... 401/125 |
| 2,557,141 | A | * | 6/1951 | Rebora ........................ 206/484 |
| 2,933,751 | A | * | 4/1960 | Brownstein ................. 401/123 |
| 4,844,251 | A | * | 7/1989 | Gueret ........................ 206/229 |
| 5,324,130 | A | * | 6/1994 | DeJean, Jr. ................. 401/131 |
| 5,660,273 | A | * | 8/1997 | Discko, Jr. ................. 206/15.3 |
| 6,387,068 | B1 | * | 5/2002 | Naughton .................... 401/125 |
| 6,450,717 | B1 | | 9/2002 | Salz et al. |

FOREIGN PATENT DOCUMENTS

| DE | 19 60 074 | 6/1971 |
| EP | 1 153 579 A2 | 11/2001 |

* cited by examiner

Primary Examiner—Tuan Nguyen
(74) Attorney, Agent, or Firm—John C. Thompson; Alan S. Korman

(57) ABSTRACT

An application apparatus for facilitating the application of a substance on an application location by a substance transfer element includes a base body, a first receptacle supported on the base body for retaining therein a fluid which can react with another material composition to form the substance to be applied, and a second receptacle supported on the base body. The second receptacle receives and retains therein the substance transfer element during stockage of the application apparatus. During a substance applying use, the substance transfer element is removed from the second receptacle with the material composition releasably retained on the substance transfer element, inserted into the first receptacle for reactive contact of the material composition with the fluid into the first receptacle to form the substance to be applied, removed from the first receptacle, and put in contact with the application location such that the substance is transferred to the application location.

18 Claims, 2 Drawing Sheets

APPLICATION APPARATUS FOR HOLDING IN READINESS A SUBSTANCE TO BE APPLIED

CROSS-REFERENCE TO RELATED APPLICATIONS

This application claims foreign priority benefits under 35 U.S.C. §119(a)-(d) from German patent application ser. no. P 103 12 454.3 filed Mar. 20, 2003.

TECHNICAL FIELD

The present invention relates generally to an application apparatus for facilitating the application of a substance on an application location by a substance transfer element, the apparatus including a base body, a first receptacle supported on the base body for retaining therein a fluid which can react with another material composition to form the substance to be applied, and a second receptacle supported on the base body.

BACKGROUND OF THE INVENTION

Application apparatus of the type to which the present invention relates is disclosed, for example, in EP-A2 1 153 579. This application apparatus comprises a base body in whose receptacle a substance is received. Following the removal of a cover foil, the substance can be accessed and can be removed with the assistance of an applicator.

It is frequently necessary in a dental practice to use substances comprised of two different material compositions or components, which must be maintained separate from one another before the substance is applied. In this connection, one configuration of the above-noted publication provides two chambers which are covered by foil which can be punctured. A similar configuration is, to be sure, well known as is disclosed, for example, in DE-PS 19 60 074.

One of the components of the substances to be applied is frequently a fluid or, at least, a viscous component, and the other component is in powder form. U.S. Pat. No. 6,450,717 discloses an improved configuration of the type of application apparatus constituted in this manner. In this improved configuration, a working end of the applicator is provided with one component of a substance to be formed which is wetted as a consequence of dipping or submersing the applicator in the other respective component which forms the substance. The configuration is suitable if the other substance component is a liquid. The application apparatus disclosed in this publication engenders, however, comparatively high work tool costs, in that three synthetic molds must be separately produced. Two of the three molds cannot be configured without an undercut, so that a valve must also be used in connection with the work tools. For this reason alone, the work tool costs ratchet significantly upward. It would, however, be desirable to have ready, for various amounts of substances, differing application apparatus. The configuration disclosed in U.S. Pat. No. 6,450,717 due to the reason of the high work tool cost, only permits recourse to one—and, indeed, a relatively large size which makes the production of this one-time use product comparatively expensive and requires more synthetic material than would actually be required.

Moreover, the application apparatus disclosed in U.S. Pat. No. 6,450,717 is, basically, only particularly hand-maneuverable if it is firmly held. A non-gripped, set down placement of the application apparatus requires either a special stand or engenders the risk that the application apparatus will tip and, consequently, lead to loss of the liquid, if the application apparatus has already been opened.

One can provide, in fact, a continuous peripheral edge along the base of this known application apparatus in order to increase its set down placement stability. This, however, would worsen the hand maneuverability of the application apparatus and would require the use of still additional synthetic masses.

The application apparatus disclosed in EP-A2 1 153 579 provides a side hand grip. This application apparatus, as well, nonetheless tends to disadvantageously promote a shaking out of the substance retained therein if the application apparatus has been disposed on a base after the cover foil has been opened.

OBJECTS AND SUMMARY OF THE INVENTION

The present invention provides a solution to the challenge of providing an application apparatus which can be produced in a cost-favorable manner to accommodate differing dosing requirements and which is clearly an improved application apparatus with respect to providing an ergonomic hand grip.

Surprisingly, the inventive application apparatus ensures an improved hand maneuverability despite the reduced work tool cost involved in its manufacture. The inventive arrangement of two receptacles adjacent one another offers, at a minimum, the possibility of an enlarged set down placement surface so that, as a basic principle, the set down placement surface is already of a larger size as compared to conventional application apparatus.

In one advantageous embodiment of the present invention, the application apparatus comprises a base plate serving the double function of being a set down placement surface having a significant dimension, and being a hand grip element. It is particularly advantageous, however, that one of the receptacles—namely, the second receptacle—is compatibly configured with respect to the working end, or of a portion of the working end, of the applicator for the receipt of the same therein. The applicator can be realistically stored in the second receptacle and, if it already has been wetted, is received in a secure and efficacious manner in the second receptacle, due to the compatible configuration thereof. From the point of view of a particularly favorable deployment of the inventive application apparatus, the application apparatus can be configured as a single dose unit, whereby the receipt of the applicator in one receptacle permits one of the substance components—namely, the respective substance component which has already been applied to the working end of the applicator—to be stored in a protective manner by virtue of the disposition of the applicator in the one receptacle and to be activated, as required, by virtue of dipping or submersing the applicator in the fluid retained in the other receptacle.

Even in a configuration in which the applicator has a significantly long shaft of, for example, more than approximately 10 cm, the inventive application apparatus can still be set down in a stable position. In an advantageous embodiment of the application apparatus of the present invention, a base body is provided which is operable to receive an insert in which the fluid has been disposed. This configuration permits, as required, that solely the insert and the applicator need be exchanged for a new respective insert or applicator. In spite of its characteristic as a single dose unit, this configuration provides the possibility to re-use the socket and the base body of the application apparatus.

Both the first receptacle as well as the second receptacle can, as needed, be configured to be re-closable. The first receptacle is covered with a cover foil and, in connection with a corresponding securement of the cover foil to the receptacle by means of an adhesive edge, a reclosable configuration can be achieved. The applicator preferably comprises a sealing arrangement and, via compatible configuration of the application element relative to the second receptacle, a closure arrangement and, as needed, even a sealing arrangement which is effective following re-insertions of the application element into the receptacle, are achievable.

It is particularly advantageous that the inventive application apparatus, in spite of its relatively large set down placement surface, has a compact configuration. The stockage of the application apparatus for transport purposes and for holding in readiness the substance to be applied can, without further measures, be effected by, for example, placement of the next following application apparatus onto the grip region of the respective application apparatus such that the application apparatus are disposed in a serial manner.

It is also especially advantageous if a closed chamber is automatically formed by the second receptacle, upon receiving the applicator inserted therein. The second component of the substance can also be in the manner of a laminarly-applied substance or, even, a not totally solid substance, which has been applied to the working end of the applicator. By virtue of the chamber characteristic of the second receptacle having the inserted applicator therein, no danger exists that the substance component on the application element will dry out even if the application element is to be stored in the second receptacle for a relatively long time. At the same time, the bristles or similar elements provided on the working end of the applicator act in the manner of a space maintaining element or spacer so that the receptacle itself is not sullied or contaminated by the respective substance component on the working end of the applicator.

It is, additionally, especially advantageous if the first receptacle is configured to be relatively higher than the second receptacle. This permits the dentist or dental technician to dip or submerge the applicator in the fluid in an effectively blind manner, as the first receptacle in which the fluid is retained is elevated while, due to relative height differential, the second receptacle gives the impression of being a subordinated structure and so it is readily apparent that the second receptacle is designated for stockage of the application element.

Via configuration of the first receptacle with a height/diameter relationship of approximately 2:1, the tendency toward a shaking or spilling out of the substance is reduced. On the other hand, radiused edges can be readily configured on the application apparatus and, in fact, inner radiused edges can be configured below, and outer radiused edges can be configured on, the access aperture. The harmonious profile of the first receptacle permits, as well, complete consumption of the respective fluid retained therein.

Additionally, the receptacles can be provided in an ergonomically favorable spacing arrangement relative to one another. A compact arrangement of the socket offers, however, the possibility to provide a spacing of, for example, approximately the diameter of the first receptacle, between the receptacles. Via the identical orientation of the two receptacles to one another in a manner in which their central longitudinal axes extend parallel to one another, the applicator can be disposed in the same manner and with the same hand movement into the first receptacle as well as into the second receptacle. Even in the event of an effectively blind placement of the application element into one of the first and second receptacles, the dentist or dental technician is able to determine, by virtue of the differing heights of the first and second receptacles, that the applicator has been placed in the appropriate receptacle.

The above-noted configuration of the first receptacle with the height/diameter relationship of 2:1, which can, as desired, also be configured instead with a height/diameter relationship of, for example, 1.5:1 or 2.5:1, ensures the stability of the application apparatus during the time, as well, when the applicator is disposed in the first receptacle. It is especially advantageous, from an ergonomics viewpoint, if the first receptacle is centrally disposed on the base body. The base plate extends beyond the side of the socket opposite to the side of the second receptacle which is adjacent the first receptacle. Due to the central arrangement, the application apparatus is optimally supported in each direction in the event of an effectively blind placement of the applicator in the course of which the application element is moved at an angled or inclined orientation toward the respective first or second receptacle of the application apparatus chosen to receive the application element.

Also, the tear-off latch or tab of the cover foil can preferably project toward the grip region of the application apparatus to facilitate the engagement thereof for the purpose of tearing off the cover foil. The cover foil is preferably formed with a resistance to tearing which clearly exceeds the magnitude of the adhesive force of the weld or adhesive seam which secures the cover foil to the respective receptacle. It is especially favorable if an adhesive seam is provided in an encircling manner around an insert of the first receptacle in order, on the one hand, to provide an air-tight disposition and, on the other hand, to make possible a re-closing of the receptacle via use of a corresponding adhesive substance. It is to be understood that a substance can be deployed as the adhesive means which is compatible with the fluid retained in the receptacle.

It is to be understood that the inventive application apparatus can be used for any suitable desired substances. Fluids such as, for example, an ethanol-water mixture or, as well, a solvent, can be deployed while the working end of the applicator can be coated with any suitable desired reaction component which is then activated or fluidized if the applicator is dipped or submerged in the fluid.

It is to be understood that, in lieu of a fluid, a viscous material or, for example, a shakable powder, can be deployed without re-configuration of the application apparatus. It is particularly advantageous if the cover foil has a comparatively high resistance to tearing. This prevents, on the one hand, a tearing of the cover foil due to an inadvertent pull on the latch and, most importantly, on the other hand prevents the working end of the application element from puncturing through the cover foil, as in such event, a portion of the respective substance component carried on the working end of the application element will transfer to, and remain hanging on, the cover foil and the mixture ratio will be different than is otherwise desired.

Further advantages, details, and features of the application apparatus of the present invention are set forth in the hereinafter following description of an embodiment of the application apparatus with reference to the figures of the drawings.

DETAILED DESCRIPTION

Figure 1:
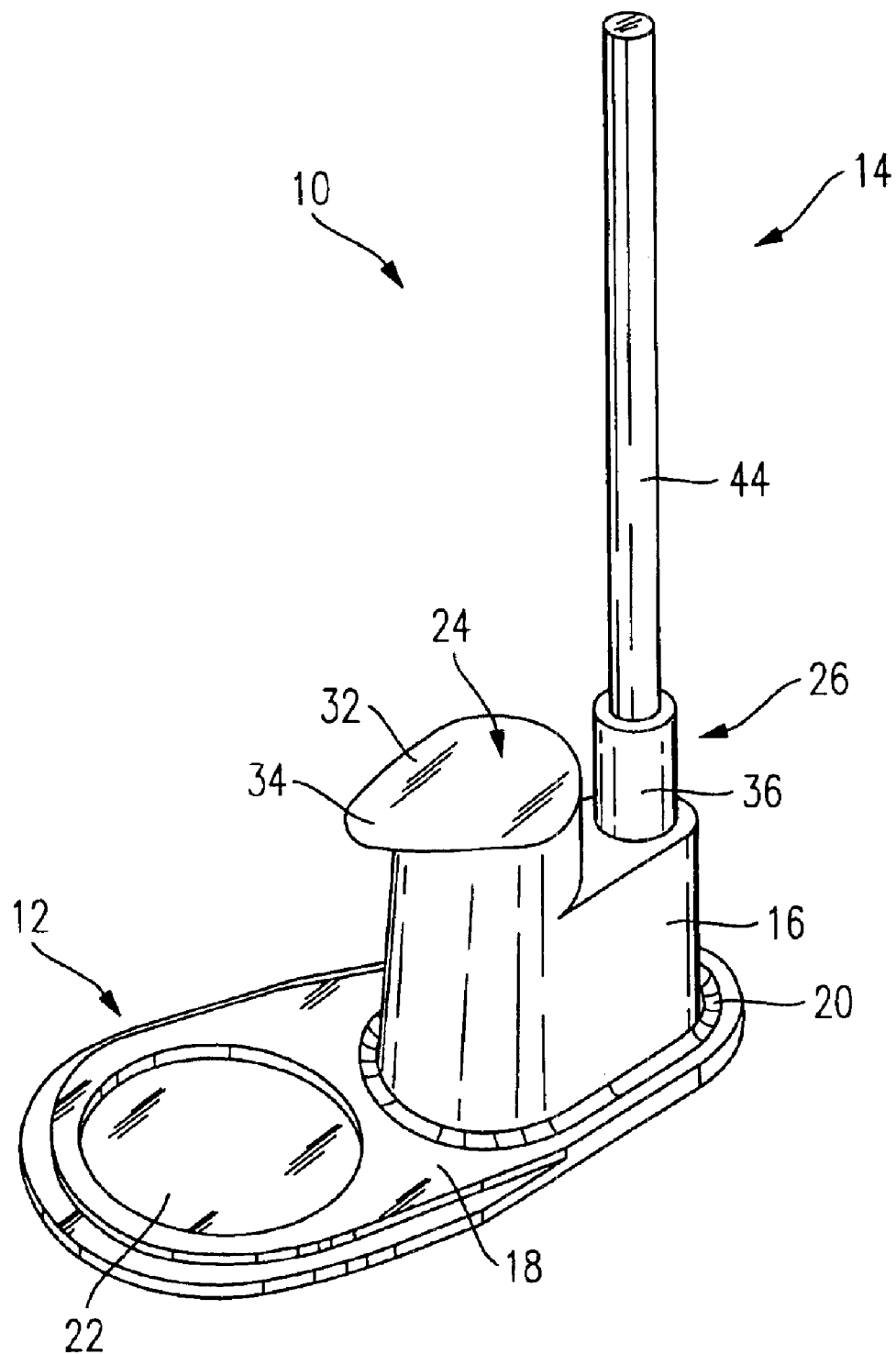
FIG. 1 is a perspective schematic view of one embodiment of the application apparatus of the present invention.

FIG. 1 shows one embodiment of the application apparatus 10 of the present invention, which is comprised substantially of a base body 12 and an application element or applicator 14 which may be carried by the base body 12, but which is removed during use. The base body 12 comprises a socket 16 which projects upwardly from a base plate 18 when the parts are in their normal working position shown in FIG. 2. A channel 20, configured as a capture rim, is disposed adjacent the socket 16 and captures the remnants of the substance which are occasionally spilled as the applicator 14 is moved away from the socket 16.

The base plate 18 is, in the illustrated embodiment, configured slightly asymmetrically. The socket 16 is disposed in the rear half of the base plate and is encircled by an edge of the base plate 18 which is comprised of a comparatively small width of, for example, 2 to 10 mm. In contrast, the front half of the base plate is substantially enlarged. It comprises, in the illustrated embodiment, an annular recess defining a grip region 22. The front half forms a projection, as viewed with respect to the socket 16, and extends in a substantially semi-annular shape having a width and depth of approximately the same dimension.

The configuration of the one embodiment of the application apparatus permits the area around the socket 16, which is available for hand-gripped movement of the application apparatus in narrow quarters such as, for example, in the proximity of the mouths of patients, to be maintained slim and small. Due to the lateral or side widening of the projection of the base plate 18 in the grip region 22, a set down position stability is nonetheless ensured.

It is to be understood that the grip region 22 can be configured in any suitable desired manner such as, for example, of a right angled shape or a quadratic shape, each such shape having rounded-off corners. Also, it is possible to provide, in lieu of a closed grip plate, a grip plate having through apertures.

Figure 2:
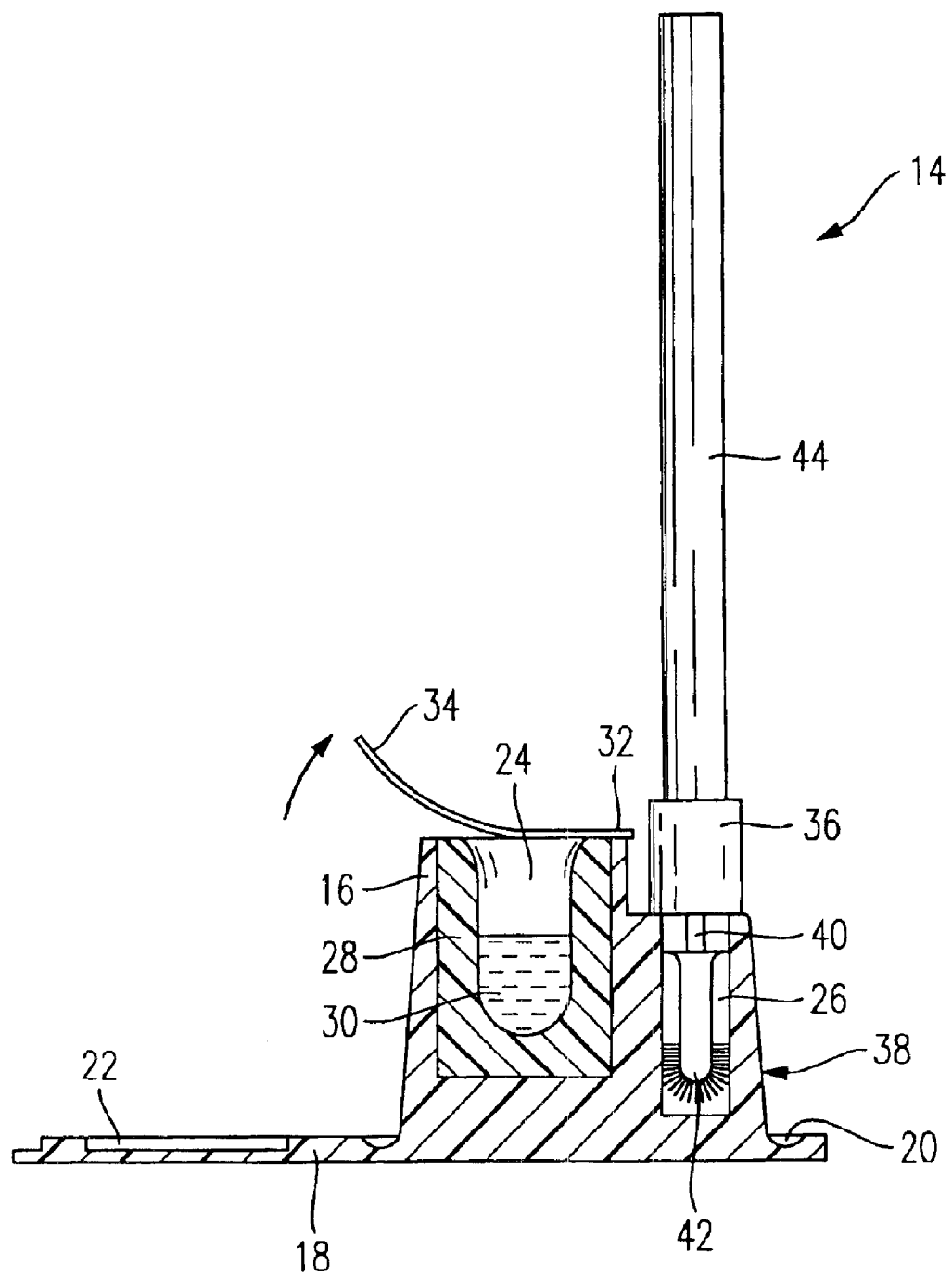
FIG. 2 is a sectional view of the one embodiment of the application apparatus shown in FIG. 1.

The socket 16 of the one embodiment of the application apparatus comprises a first receptacle 24 and a second receptacle 26 as can be seen particularly well in FIG. 2.

The first receptacle 24 is provided with an insert 28. The insert 28 is—as can be clearly seen in FIG. 2—inserted in a flush manner into the socket 16. The insert comprises a bulging, substantially deep extent which, in accordance with the invention, is designated for the receipt of a fluid 30. The fluid 30 is retained solely in the lower half of the first receptacle 24, which is configured as a bulging depth receptacle, while the upper half of the first receptacle remains unfilled.

The first receptacle 24 is, before deployment of the substance, closed off in a sealed manner by a cover foil 32. The cover foil is fused to the insert in a conventional annular ring configuration. The cover foil comprises a grip tab or latch 34 which extends to the grip region 22 and which permits tearing or pulling off of the cover foil 32.

The first receptacle 24 has approximately double the diameter of the second receptacle 26. The second receptacle 26 is configured for the insertion thereinto of the applicator 14 and is correspondingly configured for this purpose. The second receptacle comprises a substantially cylindrical cross-section and is configured in the manner of a blind hole. The second receptacle has a height/diameter relationship of approximately 4:1, whereby it is to be understood that the exact configuration can be adjusted through a wide range to accommodate the operational requirements. In the illustrated embodiment, the applicator 14 includes a neck 40 intermediate a widened element 36, which serves as the guide region, and a working end 38, the neck 40 having an outer diameter which fits exactly flush in the second receptacle 26 and which, upon insertion of the applicator 14 into the second receptacle 26, cooperates with the widened element 36 to seal off the upper end of the second receptacle 26.

The working end 38 of the applicator 14 is provided with a substance transfer element 42 which can be configured in any suitable desired manner. For example, the substance transfer element 42 can be configured as a brush, as bristles, as flocking, or as a sponge, and is preferably coated with a first component of the substance which is to be applied. Upon dipping or submersion of the working end 38 of the applicator into the fluid 30, which is a second component of the substance to be applied, a chemical reaction occurs between the first component of the substance which has previously been applied on the working end 38 of the applicator and the second component or fluid 30 such that the chemical reaction results in the creation of the desired substance to be applied.

The applicator 14 is configured in an ergonomically favorable manner while, nonetheless, having a slim shape. In this connection, the applicator includes a gripping end in the form of a shaft 44 which is grippable by hand.

In connection with the use of the application apparatus 10, the application apparatus 10 is initially disposed onto a base or counter. The socket 16 is held between two fingers and, via gripping and pulling the latch 34, the cover foil 32 is pulled off. The securement force which retains the insert 28 in the socket 16 is chosen to be of a sufficient magnitude such that the insert remains in the socket during pulling off or removal of the cover foil 32. The applicator 14 is then removed from the second receptacle 26 and is disposed into the first receptacle 24.

The dimensions of the applicator 14 and the first receptacle 24 are compatibly selected such that the applicator 14 can also be inserted and retained in a stable manner in the first receptacle 24. In this connection, it is advantageous to maintain the configuration of the first receptacle 24 as a relatively slim configuration—that is, with a comparatively large height/diameter relationship. Alternatively, it is also possible to select the height of the first receptacle 24 such that, upon insertion of the applicator 14 into the first receptacle, the applicator lies against the region of the widened element 36 such that the applicator 14 is supported in a favorable manner from the side.

Preferably, while in this position, the application apparatus can be brought into proximity of the application location—that is, in proximity to the mouth of the patient, via gripping of the grip region 22 or the shaft 44 between the thumb and index finger of, for example, the left hand of the user. The substance which has now been mixed in its final form via the reaction of the fluid 30 with the component on the substance transfer element 42 can now be transferred to the application location by means of the applicator in an ergonomically favorable manner from a position immediately adjacent the application location.

Following the application of the substance onto the application location, the application apparatus 10 can again be placed onto the planar base or counter. In order to avoid a drying out of the substance during the intermediate storage of the substance, the applicator 14 is inserted into the second receptacle 26 wherein it is sealed off against the exterior. The first receptacle 24 also permits the storage therein of the applicator. As can be seen from FIG. 2, the first receptacle (24) and the second receptacle (26) are spaced from one another and each has a central longitudinal axis with the central longitudinal axes of the first receptacle (24) and of the second receptacle (26), preferably, being substantially parallel to one another.

Preferably, a substantially thick aluminum foil is used as the cover foil 32 of the first receptacle, which foil should not be an elastically deformable foil such as the foil of the type used for a compound foil application, in order to facilitate a re-closing of the receptacle. Alternatively, in connection with, for example, the use of a compound foil having a comparatively good tearing resistance in relation to its material strength, an adhesive edge can be formed between the access aperture of the first receptacle 24 and the cover foil to thereby make possible a short term intermediate storage capability.

In a further embodiment of the application apparatus of the present invention, a weld seam in an annular shape is disposed between the cover foil 32 and the insert 28 and is encircled by an adhesive seam between the cover foil 32 and the socket 16. In this configuration, a re-closing of the receptacle is possible. This configuration ensures that dislodged portions of the adhesive seam are prevented from contaminating the retained fluid 30 during long term stockage of the application apparatus while nonetheless permitting an intermediate closure of the application apparatus in connection with a premature storage event as a result of less than complete consumption of the substance.

While a preferred form of this invention has been described above and shown in the accompanying drawings, it should be understood that applicant does not intend to be limited to the particular details described above and illustrated in the accompanying drawings, but intends to be limited only to the scope of the invention as defined by the following claims. In this regard, the term "means for" as used in the claims is intended to include not only the designs illustrated in the drawings of this application and the equivalent designs discussed in the text, but it is also intended to cover other equivalents now known to those skilled in the art, or those equivalents which may become known to those skilled in the art in the future.

What is claimed is:

1. An application apparatus (10) for facilitating the application of a substance on an application location; the application apparatus (10) comprising:
   an elongated applicator (14) having a gripping end (44) and a working end (38), the working end being provided with coating of a first component of the substance to be applied; and
   a base body (12) having
      a first receptacle (24) operable to retain therein a fluid (30) which is a second component of the substance to be applied, and
      a second receptacle (26) supported on the base body (12) next to the first receptacle (24) and having an access aperture, the second receptacle (26) being operable to receive therein the working end (38) of the substance transfer element (42) during stockage of the application apparatus (10) prior to its substance applying use.

2. The application apparatus (10) according to claim 1, wherein the second receptacle (26) forms a stand for the applicator (14), and wherein the base body (12) is configured to support the application apparatus (10) in a stable manner on a horizontal surface while the applicator (14) is in the stand alone support position in the second receptacle (26).

3. The application apparatus (10) according to claim 1, wherein the first receptacle (24) and the second receptacle (26) are spaced from one another and each has a central longitudinal axis with the central longitudinal axes of the first receptacle (24) and of the second receptacle (26) being substantially parallel to one another.

4. The application apparatus (10) according to claim 1, wherein the base body (12) includes a socket (16).

5. The application apparatus (10) according to claim 4, wherein at least one of the first receptacle (24) and the second receptacle (26) includes an insert (28) operable to be seated in the socket (16).

6. The application apparatus (10) according to claim 4, wherein the base body (12) includes a base plate (18) on which the socket (16) is mounted, the base plate (18) having a layout extent, as viewed in the direction perpendicular to the height of the socket (16), substantially greater than the layout extent of the socket (16), the layout extent of the base plate (18) being formed by a projection of the base plate (18).

7. The application apparatus (10) according to claim 6, wherein the projection of the base plate (18) is configured as a hand grippable portion and includes a recess.

8. The application apparatus (10) according to claim 4, wherein a fluid capture rim (20) encircles the socket (16) for capturing fluid spillage.

9. The application apparatus (10) according to claim 4, wherein the base body (12) includes a base plate (18) on which the socket (16) is mounted, the base plate (18) having a height of between 1 and 10 mm and die socket (16) having a height of between 15 and 60 mm.

10. The application apparatus (10) according to claim 4, wherein the base body (12) includes a base plate (18) on which the socket (16) is mounted and the respective access apertures of the first receptacle (24) and the second receptacle (26) are at different heights relative to one another.

11. The application apparatus (10) according to claim 4, wherein the base body (12) includes a base plate (18) on which the socket (16) is mounted and the applicator (14) includes a widened portion (36) supported in the access aperture of the second receptacle (26) on the side of the socket (16) opposite to the base plate (18).

12. The application apparatus (10) according to claim 11, wherein the diameter of the access aperture of the second receptacle (26) substantially corresponds to the respective diameter of the substance transfer element (42) at the region of the substance transfer element (42) in the direction of the working end (38) at which the widened portion (36) is located.

13. The application apparatus (10) according to claim 4, wherein the first receptacle (24) includes an insert (28) forming the fluid retaining volume of the first receptacle (24) and a removable cover foil (32) for covering the access aperture of the first receptacle (24), the cover foil (32) being secured to the access aperture of the first receptacle (24) by a welded seam which encircles the access aperture.

14. The application apparatus (10) according to claim 13, wherein the cover foil (32) includes a latch (34) operable to be hand-gripped for pulling the cover foil (32) to open the access aperture of the first receptacle (24), the latch (34) projecting laterally beyond first receptacle preferably, projecting laterally beyond the socket (16).

15. The application apparatus (10) according to claim 1, wherein the second receptacle (26) is substantially in the configuration of a blind hole.

16. The application apparatus (10) according to claim 1, wherein the first receptacle has a closed lower end which is rounded.

17. The application apparatus (10) according to claim 1, wherein the first receptacle (24) has a height to diameter relationship of more than 1.5:1.

18. The applicator apparatus according to claim 1 wherein the elongated applicator is provided with a widened element and a neck (40) located between the gripping end (44) and the working end (38), the neck having an outer diameter which fits exactly flush in the second receptacle (26) and which, upon insertion of the applicator (14) into the second receptacle (26), cooperates with the widened element (36) to seal off the upper end of the second receptacle (26).

* * * * *